US010624836B2

(12) United States Patent
Eilstein et al.

(10) Patent No.: US 10,624,836 B2
(45) Date of Patent: Apr. 21, 2020

(54) ESSENTIAL OIL OF ACHILLEA AS ANTI-AGEING AGENT

(71) Applicant: L'OREAL, Paris (FR)

(72) Inventors: Joan Eilstein, Paris (FR); Corinne Ferraris, Crest (FR)

(73) Assignee: L'OREAL, Paris (FR)

( * ) Notice: Subject to any disclaimer, the term of this patent is extended or adjusted under 35 U.S.C. 154(b) by 253 days.

(21) Appl. No.: 15/031,758

(22) PCT Filed: Oct. 21, 2014

(86) PCT No.: PCT/IB2014/065491
§ 371 (c)(1),
(2) Date: Apr. 25, 2016

(87) PCT Pub. No.: WO2015/059627
PCT Pub. Date: Apr. 30, 2015

(65) Prior Publication Data
US 2016/0263011 A1 Sep. 15, 2016

(30) Foreign Application Priority Data
Oct. 23, 2013 (FR) ..................... 13 60310

(51) Int. Cl.
A61K 8/92 (2006.01)
A61Q 19/08 (2006.01)
A61K 8/35 (2006.01)
A61K 8/49 (2006.01)
A61K 8/02 (2006.01)
A61K 8/31 (2006.01)
A61K 8/34 (2006.01)
A61K 8/37 (2006.01)
A61K 8/38 (2006.01)

(52) U.S. Cl.
CPC ............ *A61K 8/922* (2013.01); *A61K 8/0216* (2013.01); *A61K 8/31* (2013.01); *A61K 8/34* (2013.01); *A61K 8/35* (2013.01); *A61K 8/37* (2013.01); *A61K 8/38* (2013.01); *A61K 8/498* (2013.01); *A61Q 19/08* (2013.01); A61K 2236/37 (2013.01); A61K 2800/596 (2013.01); A61K 2800/70 (2013.01)

(58) Field of Classification Search
None
See application file for complete search history.

(56) References Cited

U.S. PATENT DOCUMENTS

2010/0034763 A1 2/2010 Madison
2015/0086498 A1* 3/2015 Lerebour ................. A61K 8/35
424/65

FOREIGN PATENT DOCUMENTS

| JP | H02-295912 A | 12/1990 |
| JP | 2001-114637 A | 4/2001 |
| JP | 2010-280572 A | 12/2010 |
| JP | 2013-087058 A | 5/2013 |
| WO | 01/066079 A1 | 9/2001 |

OTHER PUBLICATIONS

Pain et al., "Surface rejuvenating effect of Achillea millefolium extract", Int. J. Cosm. Sci., 2011, vol. 33, pp. 535-542 (Year: 2011).*
Mohammadhosseini et al., "Chemical composition of the essential oils and extracts of *Achillea* species and their biological activities: A review", Journal of Ethnopharmacology, 2017, vol. 199, pp. 257-315 (Year: 2017).*
Feb. 6, 2015 International Search Report issued in International Patent Application No. PCT/IB2014/065491.
Apr. 26, 2016 International Preliminary Report on Patentability issued in International Patent Application No. PCT/IB2014/065491.
Canan Karamenderes et al. "Composition and Antimicrobial Activity of the Essential Oils of Some *Achillea* L. Species in Turkey". Acta Pharmaceutica Sciencia, Istanbul, vol. 44, No. 3, Jan. 1, 2002, pp. 221-225.
K.H.C. Baser et al. "Composition of the Essential Oils of Two Endemic Species From Turkey: Achillea lycaonica and A. ketenoglui". Chemistry of Natural Compounds, Kluwer Academic Publishers-Consultants Bureau, NE, vol. 37, No. 3, May 1, 2001, pp. 245-252.
Z. Boskovic et al. "Essential Oil Composition of Four *Achillea* Species From the Balkans and Its Chemotaxonomic Significance". Chemistry of Natural Compounds, Kluwer Academic Publishers-Consultants Bureau, NE, vol. 41, No. 6, Nov. 1, 2005, pp. 674-678.
Chinese Traditional and Herbal Drugs, 13, 174-187 (Translation of Abstract).

* cited by examiner

*Primary Examiner* — Jeffrey S Lundgren
*Assistant Examiner* — Stephanie K Springer
(74) *Attorney, Agent, or Firm* — Oliff PLC

(57) ABSTRACT

The present invention relates to the cosmetic use of an essential oil of *Achillea*, as an active agent for preventing and/or treating the signs of skin ageing, characterized in that this essential oil of *Achillea* comprises the following compounds, each present at more than 5% by weight relative to the total weight of the essential oil: *artemisia* ketone, chrysanthenone (two combined isomers), and ascaridole. It also relates to the associated cosmetic process.

11 Claims, 1 Drawing Sheet

ESSENTIAL OIL OF ACHILLEA AS ANTI-AGEING AGENT

The present invention relates to the field of cosmetic products, more particularly intended for the treatment and/or prevention of the signs of skin ageing.

More particularly, the present invention aims to propose the use of an active agent for preventing and/or treating the signs of skin ageing.

It also relates to a non-therapeutic cosmetic process for treating and/or preventing the signs of skin ageing, comprising the topical application to the skin of a composition comprising said active agent.

The term "skin" is intended to mean all of the skin of the body, including the scalp, the mucous membranes, the semi-mucous membranes, and the skin appendages.

The term "skin appendages" is intended to mean the body hair, the eyelashes, the hair and the nails. More particularly, in the present invention, the skin of the neckline, of the neck and of the face, and in particular the skin of the face, are considered.

Human skin consists of several compartments, three of which cover the whole of the body, namely a superficial compartment, which is the epidermis, the dermis and a deep compartment, which is the hypodermis.

The epidermis is a keratinized, stratified pavement epithelium. It consists mainly of keratinocytes, but also of other cells, and lies on a basal membrane which separates it from the dermis.

The dermis is a connective tissue. Its architecture results from the organization and interactions between the constituents of the extracellular matrix and the fibroblasts which ensure their synthesis and their degradation. It constitutes the principal mass of the skin. The dermis is subdivided into two layers, the papillary layer and the reticular layer. The dermis consists of collagen (mainly I and III) fibres and elastic fibres and also glycosaminoglycans and proteoglycans. These various structures form a complex network which plays a key role in the biomechanical properties of the skin.

The dermo-epidermal junction (DEJ) or basal membrane consists of leaflets of extracellular matrix separating cells of different origin: keratinocytes and fibroblasts. Among the main constituents of this DEJ is collagen IV.

Finally, the hypodermis essentially consists of a type of cells that are specialized in the accumulation and storage of fats, the adipocytes.

Among the causes of the appearance of the signs of skin ageing are oxidative stress and modification of the DEJ.

Oxidative stress, which can be both of endogenous origin, via mitochondria, and of exogenous origin, via exposure to UV radiation, generating an exacerbated production of free radicals, causes in particular elastosis, an early appearance of wrinkles and also the formation of wizened skin.

The consequence of modification of the DEJ is a loss of firmness and of elasticity of the skin.

There is a need to have new active agents capable of combating the signs of skin ageing, of maintaining and/or restoring the viscoelastic or biomechanical properties of the skin, in particular of improving the firmness, the elasticity and the tonicity of the skin, or else of combating oxidative stress and of preventing the appearance of the signs of photoageing of the skin.

There remains more specifically a need for new active agents capable of exerting a cosmetic action making it possible both to maintain the quality of the DEJ and to stimulate the antioxidant defences of cells.

The object of the present invention is to meet these needs.

Thus, according to a first subject, the present invention relates to the cosmetic use of an essential oil of *Achillea*, as an active agent for preventing and/or treating the signs of skin ageing, characterized in that this essential oil of *Achillea* comprises the following compounds, each present at more than 5% by weight relative to the total weight of the essential oil:
  *artemisia* ketone,
  chrysanthenone (two combined isomers), and
  ascaridole.

The term "essential oil of *Achillea*" is intended to mean an essential oil of *Achillea* sp. and/or hybrids thereof.

Preferably, the essential oil of *Achillea* according to the invention is an essential oil of *Achillea* sp.

One of the advantages of the invention is to provide a natural active agent.

Surprisingly, the inventors have noted that the use of the essential oil of *Achillea*, in particular the essential oil of *Achillea* sp., according to the invention generates a significant increase in collagen IV production by primary normal human keratinocytes, thus making it possible to maintain the quality of the DEJ.

Further more, the inventors have noted that the use of this essential oil, in particular the essential oil of *Achillea* sp., also makes it possible to increase the intra-tissue glutathione concentration.

The skin has various inducible, enzymatic and non-enzymatic, endogenous antioxidant protection systems. The intracellular universal non-enzymatic antioxidant is glutathione (GSH): through its thiol function, this tripeptide is capable of neutralizing reactive oxygen species. Glutathione is also the cofactor of antioxidant and detoxification enzymes such as glutathione peroxidase (Gpx) or glutathione-S-transferase.

Increasing the glutathione concentration consequently stimulates the antioxidant defences of cells and thus makes it possible to prevent and/or treat the signs of skin ageing.

The essential oil of *Achillea* used according to the invention, preferably the essential oil of *Achillea* sp., may also comprise the following compounds, preferably each present in a content ranging from 3% to 10% by weight relative to the total weight of the essential oil:
  para-cymene,
  1,8-cineole and beta-phellandrene, and
  camphor.

More particularly, the essential oil of *Achillea* used according to the invention, preferably the essential oil of *Achillea* sp., comprises the following compounds, each present at more than 6% by weight relative to the total weight of the essential oil:
  *artemisia* ketone,
  chrysanthenone (two combined isomers), and
  ascaridole.

According to one particular embodiment, the essential oil used according to the invention, preferably the essential oil of *Achillea* sp., also comprises the following compounds, each present at concentrations of greater than 1% by weight relative to the total weight of the essential oil, in particular between 1% and 5% by weight:
  camphene,
  yomogi alcohol,
  alpha-thujone,
  artemisyl acetate, and
  isoascaridole.

Likewise according to this first aspect, the present invention aims to protect the cosmetic use of an essential oil of

*Achillea*, preferably the essential oil of *Achillea* sp., as previously defined, as an active agent for preventing and/or treating the signs of skin ageing, the latter being chosen from dull, lifeless skin, wrinkles and/or fine lines, thinning of the skin, loss of firmness and/or of elasticity and/or of tonicity and/or of suppleness of the skin and/or slackening of the skin.

In particular, the signs of skin ageing may be induced by extrinsic ageing, in particular photoageing, or else induced by chronological ageing.

The present invention also relates to the cosmetic use as previously defined, in which said essential oil is used in a cosmetic composition, in particular intended for preventing and/or treating the signs of skin ageing.

The present invention is also directed towards a non-therapeutic cosmetic process for preventing and/or treating the signs of skin ageing, comprising at least one step of topical application to the skin of a composition comprising at least one essential oil of *Achillea* as previously defined, preferably the essential oil of *Achillea* sp.

In the context of the present invention, the term "viscoelastic or biomechanical properties of the skin" is intended to mean the extensibility, tonicity, firmness, suppleness and/or elasticity properties of the skin.

The term "signs of skin ageing" is intended to mean any modification of the external appearance of the skin due to ageing, whether chronobiological and/or extrinsic, principally photoinduced, such as, for example, wrinkles and fine lines, withered skin, flaccid skin, thinned skin, dull, lifeless skin, lack of elasticity and/or of tonicity of the skin.

This term is considered to be equivalent to the term "skin disorders induced by chronological ageing and/or extrinsic ageing".

According to the invention, the term "preventing" or "prevention" is intended to mean reducing the risk of occurrence or slowing down the occurrence of a given phenomenon, namely, according to the present invention, the signs of skin ageing.

A composition in accordance with the invention, namely intended for the implementation of the invention, is a cosmetic composition and therefore comprises a physiologically acceptable medium.

The term "physiologically acceptable medium" is intended to mean a medium that is compatible with all keratin materials such as the skin, the scalp, the nails, mucous membranes, the eyes and the hair, or any other area of body skin. A physiologically acceptable medium is preferentially a cosmetically or dermatologically acceptable medium, that has no unpleasant odour or appearance, and that is entirely compatible with the route of administration under consideration.

Essential Oil of *Achillea*

According to the definition given in the international standard ISO 9235 and adopted by the Commission of the European Pharmacopoeia, an essential oil is an odourous product, generally of complex composition, obtained from a botanically defined plant starting material, either by steam distillation, or by dry distillation, or by an appropriate mechanical process without heating (cold expression). The essential oil is generally separated from the aqueous phase via a physical process which does not result in any significant change in the composition.

Modes for Obtaining Essential Oils

The choice of technique depends mainly on the starting material: its original state and its characteristics, its actual nature. The "essential oil/plant starting material" yield may be extremely variable depending on the plants: 15 ppm to more than 20%. This choice conditions the characteristics of the essential oil, in particular viscosity, colour, solubility, volatility, richness or poorness in certain constituents.

Mention may be made, among the methods for obtaining an essential oil, of steam distillation, which can, for example, be carried out by dry distillation or hydrodistillation.

Hydrodistillation can be carried out on a glass apparatus, such as that defined in the European Pharmacopoeia for the determination of the essential oil from a plant material.

Steam distillation corresponds to the vaporization, in the presence of steam, of a substance which is not very miscible with water. The starting material is brought together with water brought to boiling point (hydrodistillation) or with steam in a still (dry distillation). The steam entrains the essential oil vapour, which is condensed in the condenser in order to be recovered as liquid phase in a Florentine flask (or essence jar), where the essential oil is separated from the water by settling. The aqueous distillate that remains after the steam distillation, once the separation of the essential oil has been performed, is known as the "aromatic water" or "hydrolate" or "distilled floral water".

Physicochemical Characteristics

Essential oils are generally volatile and liquid at ambient temperature, which distinguishes them from "set" oils. They are more or less coloured and their density is generally less than that of water. They have a high refractive index and most of them deflect polarized light. They are liposoluble and soluble in the usual organic solvents, steam distillable, and very sparingly soluble in water.

As previously specified, the present invention relates to the use of an essential oil of *Achillea*, as an active agent for preventing and/or treating the signs of skin ageing, characterized by the composition of said essential oil.

The essential oil of *Achillea* can be an essential oil of *Achillea* sp. and/or hybrids thereof, preferably the essential oil of *Achillea* sp.

Thus, preferably, the present invention relates to the use of an essential oil of *Achillea* sp., as an active agent for preventing and/or treating the signs of skin ageing, characterized by the composition of said essential oil.

According to one particular embodiment, the essential oil of *Achillea* used in the context of the present invention, preferably the essential oil of *Achillea* sp., comprises chrysanthenone (two combined isomers) and ascaridole, each present at more than 6% by weight relative to the total weight of the essential oil.

The harvest may advantageously be carried out at the "end of flowering" stage.

Preferably, the essential oil, in accordance with the present invention, is obtained from the aerial part of *Achillea* sp.

*Achillea* sp. is a plant of the family Asteraceae and of the genus *Achillea*.

According to the present invention, the essential oil of *Achillea* in accordance with the invention, preferably the essential oil of *Achillea* sp., may be used in an amount sufficient to obtain the desired effect, i.e. in an amount sufficient to prevent and/or treat the signs of skin ageing.

The chemical composition of the essential oil of *Achillea* in accordance with the invention thus obtained can be analyzed by conventional techniques known to those skilled in the art, such as gas chromatography GC analysis, chromatographic analysis with flame ionization detection, referred to as GC-FID, or GC/MS analysis, which consists of the use of a mass spectrometer coupled to a gas chromatograph.

An essential oil in accordance with the invention may be used as such, i.e. alone, or may be introduced into a composition, in particular a cosmetic or dermatological composition.

Composition

According to one embodiment of the invention, the essential oil of *Achillea* in accordance with the invention, preferably the essential oil of *Achillea* sp., can be incorporated into a cosmetic composition intended for preventing and/or treating the signs of skin ageing, in particular an anti-ageing composition.

Thus, the present invention is directed towards a cosmetic use in which the essential oil of *Achillea* in accordance with the invention, preferably the essential oil of *Achillea* sp., is present in a cosmetic composition, in particular intended for preventing and/or treating the signs of skin ageing. Advantageously, in this cosmetic use, said essential oil of *Achillea*, preferably the essential oil of *Achillea* sp., is present in the composition in a content ranging from 0.002% to 10% by weight, preferably from 0.02% to 1% by weight and quite preferentially from 0.05% to 0.8% by weight relative to the total weight of the cosmetic composition.

Thus, according to one particular embodiment, a composition used according to the invention comprises an essential oil of *Achillea* in accordance with the invention, preferably the essential oil of *Achillea* sp., comprising *artemisia ketone*, chrysanthenone (two combined isomers) and ascaridole, each present at more than 5% by weight relative to the total weight of essential oil, also comprising para-cymene, 1,8-cineole, beta-phellandrene and camphor, each present in a content ranging from 3% to 10% by weight relative to the total weight of the essential oil, and comprising the following compounds, each present at concentrations of greater than 0.3% by weight relative to the total weight of said oil of *Achillea*, in particular between 0.3% and 5% by weight:
   camphene,
   yomogi alcohol,
   alpha-thujone,
   artemisyl acetate, and
   isoascaridole.

The composition used according to the invention can be administered in particular topically or orally, preferably topically.

Preferably, an essential oil according to the invention, when it is present in a composition, is formulated in a physiologically acceptable medium.

When the composition is intended to be administered topically, such a medium is considered as being physiologically acceptable when it does not cause any stinging, tautness or redness that is unacceptable to the user.

Advantageously, a composition suitable for the invention, comprising an essential oil in accordance with the invention, is intended for topical administration.

A composition suitable for the invention may be in any galenical form normally used in the cosmetics fields.

It may in particular be in the form of an aqueous or aqueous-alcoholic solution, which is optionally gelled, a dispersion of the lotion type, which is optionally a two-phase lotion, an oil-in-water or water-in-oil or multiple emulsion, an aqueous gel, a gelled or non-gelled oil, a dispersion of oil(s) in an aqueous phase, in particular with the aid of spherules, these spherules possibly being polymer particles or, better still, lipid vesicles of ionic and/or non-ionic type, or alternatively in the form of a powder, a serum, a paste or a supple stick. It may be of solid, pasty or more or less fluid liquid consistency.

Thus, the composition may comprise any of the constituents normally used in the envisaged topical administration and application.

Mention may be made in particular of water, solvents, oils of mineral, animal and/or plant origin, in particular as detailed hereinbelow, waxes, especially as described hereinbelow, pigments, fillers, surfactants, thickeners, gelling agents and preservatives, and mixtures thereof.

A composition suitable for the invention may also contain various adjuvants commonly used in the cosmetics field, such as sequestering agents, odour absorbers, UV-screening agents, fragrances, matting agents, and abrasive fillers or exfoliating agents, and mixtures thereof.

A composition suitable for the invention may advantageously comprise at least one additional active agent.

The expression "additional active agent" is intended to mean, in the context of the present invention, a compound which, by itself, i.e. not requiring the intervention of an external agent to activate it, has a biological activity which may in particular be:
   a metalloproteinase (MMP)-inhibiting activity, and/or
   a photoprotective activity, and/or
   a moisturizing activity, and/or
   a muscle-relaxing or relaxing activity, and/or
   a collagen synthesis-stimulating activity, and/or
   an elastin synthesis-stimulating activity, and/or
   a glycosaminoglycan synthesis-stimulating activity, and/or
   a fibronectin synthesis-stimulating activity, and/or
   a fibroblast proliferation-stimulating activity, and/or
   a keratinocyte proliferation and/or differentiation-stimulating activity.

The additional active agent used in a composition suitable for the invention can represent from 0.0001% to 20%, preferably from 0.01% to 10% and even better still from 0.01% to 5% by weight relative to the total weight of the composition.

Moreover, a composition suitable for the invention may advantageously comprise from 5% to 80% by weight and preferably from 35% to 75% by weight of water relative to the total weight of said composition.

A composition suitable for the invention may advantageously have a firm and compact feel when taken up. It may be thick on application and then become transformed, melt and release freshness.

Needless to say, those skilled in the art will take care to select this or these optional additional compound(s), and/or the amount thereof, such that the advantageous properties of the essential oil according to the invention are not, or are not substantially, adversely affected by the envisaged addition, and such that the properties of the compositions resulting therefrom are compatible with the preferred route of administration.

A composition suitable for the invention may advantageously comprise at least one fatty phase that is liquid at ambient temperature and atmospheric pressure.

As examples of oils that may be used in a composition suitable for the invention, mention may be made of:
   hydrocarbon-based oils of animal origin, such as perhydrosqualene,
   hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil, synthetic esters and ethers, in particular of fatty acids, such as the oils of formulae $R_1COOR_2$ and $R_1OR_2$ in which $R_1$ represents an amino acid residue comprising from 8 to 29 carbon atoms, and $R_2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate, isostearyl isostearate; hydroxylated esters, such as isostearyl lactate, octylhydroxystearate, octyldodecyl hydroxystearate, diisostearyl malate, triisocetyl citrate, fatty alcohol heptanoates, octanoates and decanoates; polyol esters, such as propylene glycol dioctanoate, neopentyl glycol diheptanoate and diethylene glycol diisononanoate; and pentaerythritol esters, such as pentaerythrityl tetraisostearate, linear or branched hydrocarbons of inorganic or synthetic origin, such as volatile or non-volatile liquid paraffins, and derivatives thereof, isohexadecane, isododecane, petroleum jelly, polydecenes, and hydrogenated polyisobutene such as Parleam® oil, associated natural or synthetic essential oils, fatty alcohols containing from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol and linoleyl alcohol, partially hydrocarbon-based and/or silicone-based fluoro oils, such as those described in document JP-A-2-295 912, silicone oils, such as volatile or non-volatile polymethylsiloxanes (PDMSs) with a linear or cyclic silicone chain, which are liquid or pasty at ambient temperature, in particular cyclopolydimethylsiloxanes (cyclomethicones) such as cyclohexasiloxane and cyclopentasiloxane; polydimethylsiloxanes comprising alkyl, alkoxy or phenyl groups, which are pendent or at the end of a silicone chain, these groups containing from 2 to 24 carbon atoms; phenylsilicones, such as phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxysilicates, and polymethylphenylsiloxanes, and mixtures thereof.

In the list of the abovementioned oils, the term "hydrocarbon-based oil" is intended to mean any oil predominantly comprising carbon and hydrogen atoms, and optionally ester, ether, fluoro, carboxylic acid and/or alcohol groups.

The other fatty substances that may be present in the oily phase are, for example, waxes and fatty acids comprising from 8 to 30 carbon atoms, such as stearic acid, lauric acid, palmitic acid and oleic acid.

As waxes that may be used according to the invention, mention may be made of waxes of animal origin such as beeswax, spermaceti, lanolin wax and lanolin derivatives, plant waxes such as carnauba wax, candelilla wax, ouricury wax, Japan wax, cocoa butter, cork fibre wax or sugarcane wax, mineral waxes, for example paraffin wax, petroleum jelly wax, lignite wax or microcrystalline waxes or ozokerites, synthetic waxes, among which are polyethylene waxes, polytetrafluoroethylene waxes and the waxes obtained by Fisher-Tropsch synthesis or alternatively silicone waxes, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance the $C_{20}$-$C_{40}$ alkyl stearate sold under the trade name Kester Wax K82H by the company Koster Keunen.

These fatty substances can be chosen in a varied manner by those skilled in the art so as to prepare a composition having the desired properties, for example of consistency or texture.

The compositions suitable for the invention may comprise a volatile oil.

For the purposes of the invention, the term "volatile oil" is intended to mean an oil that is capable of evaporating on contact with keratin fibres in less than one hour, at ambient temperature and atmospheric pressure. The volatile organic solvent(s) and volatile oils of the invention are volatile organic solvents and cosmetic oils that are liquid at ambient temperature, with a non-zero vapour pressure at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

Volatile oils that may be mentioned, inter alia, include cyclic or linear silicones containing from 2 to 6 silicon atoms, such as cyclohexasiloxane, dodecamethylpentasiloxane, decamethyltetrasiloxane, butyltrisiloxane and ethyltrisiloxane. It is also possible to use branched hydrocarbons, for instance isododecane, and also volatile perfluoroalkanes such as dodecafluoropentane and tetradecafluorohexane, sold under the names PF 5050® and PF 5060® by the company 3M, and perfluoromorpholine derivatives, such as 4-trifluoromethylperfluoromorpholine sold under the name PF 5052® by the company 3M.

The amount of oily phase present in the compositions suitable for the invention may range, for example, from 0.01% to 50% by weight and preferably from 0.1% to 30% by weight relative to the total weight of the composition.

A composition suitable for the invention may advantageously be in the form of an emulsion, obtained in particular by dispersing an aqueous phase in a fatty phase (W/O) or a fatty phase in an aqueous phase (O/W), of liquid or semi-liquid consistency of the milk type, or of soft, semi-solid or solid consistency of the cream or gel type, or alternatively a multiple emulsion (W/O/W or O/W/O). These compositions are prepared according to the usual methods.

A composition of this type may be in the form of a face and/or body care or makeup product, and may be conditioned, for example, in the form of cream in a jar or of fluid in a tube or a pump-action bottle.

The emulsions suitable for the invention may comprise at least one emulsifier chosen from amphoteric, anionic, cationic and non-ionic emulsifiers, used alone or as a mixture.

Advantageously, the emulsifiers are appropriately chosen according to the emulsion to be obtained (W/O or O/W). The emulsifiers are generally present in the composition in a proportion that may range from 0.3% to 30% by weight and preferably from 0.5% to 20% by weight relative to the total weight of the composition.

Examples of emulsifiers that may be mentioned for the O/W emulsions include non-ionic surfactants, and in particular esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

A composition suitable for the invention may also comprise at least one silicone elastomer, such as the products sold under the name KSG by the company Shin-Etsu, under the name Trefil, BY29 or EPSX by the company Dow Corning, or under the name Gransil by the company Grant Industries.

A composition suitable for the invention may also comprise at least one colorant chosen, for example, from pigments, nacres, dyes and materials with an effect, and mixtures thereof.

These colorants may be present in a content ranging from 0.01% to 50% by weight and preferably from 0.01% to 30% by weight relative to the total weight of the composition.

A composition suitable for the invention may also comprise at least one filler, in particular in a content ranging from 0.01% to 50% by weight and preferably ranging from 0.01% to 30% by weight relative to the total weight of the composition.

These fillers may be mineral or organic and of any shape, platelet-shaped, spherical or oblong, irrespective of the crystallographic form (for example lamellar, cubic, hexagonal, orthorhombic or amorphous).

Mention may be made of silica, talc, mica, kaolin, lauroyllysine, starch, boron nitride, PTFE powders, PMMA powders, methylsilsesquioxane resin powders (for instance Tospearl 145A from GE Silicone), hollow silicone resin hemispherical particles (for instance NLK 500, NLK 506 and NLK 510 from Takemoto Oil and Fat), barium sulfate, precipitated calcium carbonate, magnesium carbonate, magnesium hydrogen carbonate, hydroxyapatite, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

In the case of oral administration, the composition may be in the form of tablets, gel capsules, sugar-coated tablets, syrups, suspensions, solutions, powders, granules, emulsions, suspensions of microspheres, nanospheres or lipid or polymeric vesicles allowing controlled release. Preferably, the composition is the form of a food supplement.

In the case of topical administration, the compositions according to the invention may be in the form of products for caring for the skin or semi-mucous membranes, such as a protective, treatment or care composition for the face, for the lips, for the hands, for the feet, for the anatomical folds or for the body (for example, day cream, night cream, makeup-removing cream, makeup base, antisun composition, protective or care body milk, aftersun milk, skincare or scalp-care lotion, gel or foam, serum, powder, mask, artificial tanning composition, aftershave composition, hair composition, product for the region of the armpits, or hygiene and cleansing product.

According to one preferred embodiment, a composition comprising the essential oil of the invention is formulated in an anti-ageing cream.

A composition according to the invention may be manufactured via any known process generally used in the cosmetics field.

The non-therapeutic cosmetic process of the invention is carried out by topically administering a composition comprising an essential oil of *Achillea* in accordance with the invention.

The topical administration consists of the external application to the skin of cosmetic compositions according to the usual technique for using these compositions.

By way of illustration, the cosmetic process according to the invention can be carried out by topical application, for example daily, of an essential oil of *Achillea* in accordance with the invention, which may, for example, be formulated in the form of a cream, gel, serum, lotion, emulsion, makeup-removing milk or aftersun composition.

The process according to the invention may comprise a single application.

According to another embodiment, the application is repeated, for example 2 to 3 times daily for one day or more and generally for an extended period of at least 4 weeks, or even 4 to 15 weeks, with, where appropriate, one or more periods of stoppage.

Furthermore, treatment combinations optionally with oral or topical forms may be envisaged, in order to complement or to reinforce the activity of the essential oil of *Achillea* defined by the invention.

Thus, a topical treatment with a composition containing an essential oil of *Achillea* in accordance with the invention, combined with an orally or topically administered composition optionally containing another essential oil, could be imagined.

The ingredients are mixed, before being formed, in the order and under conditions that are easily determined by those skilled in the art.

According to one particular embodiment of the invention, other agents intended to make the appearance and/or the texture of the skin more attractive may also be added to the composition according to the invention.

Throughout the description, including the claims, the expression "comprising a" should be understood as being synonymous with "comprising at least one", unless otherwise specified.

The expressions "between . . . and . . . " and "ranging from . . . to . . . " should be understood as being limits included, unless otherwise specified.

The examples that follow are presented as non-limiting illustrations of the invention.

EXAMPLES

Example 1: Production of an Essential Oil of *Achillea*

An essential oil of *Achillea* was prepared by distillation of 300 g of fresh aerial part picked at the deblossomed stage, in an apparatus of Clevenger type, by dry distillation, for 1 h 30. An essential oil was obtained with a yield of about 0.25% to 0.50%. The essential oil thus obtained contains:

| | |
|---|---|
| Ascaridole | 11.70% |
| Artemisia ketone | 33.4% |
| Chrysanthenone | 6.6% |
| Camphene | 1.2% |
| Yomogi alcohol | 1.3% |
| Para-cymene | 5.7% |
| 1,8-Cineole and beta-phellandrene | 6.3% |

-continued

| Alpha-thujone | 4.3% |
|---|---|
| Camphor | 5.3% |
| Artemisyl acetate | 1.3% |
| Isoascaridole | 1.0% |

The composition of the essential oil obtained was determined by GC and mass spectrometry.

Example 2: Effect of an Essential Oil of *Achillea* on Collagen IV Production by Primary Normal Human Keratinocytes The test which follows makes it possible to show that the essential oil of *Achillea* causes an increase in collagen IV production by primary normal human keratinocytes. This demonstration is carried out by in situ immunolabelling and image analysis.

Procedure:

The keratinocytes were seeded into and cultured in culture medium for 24 hours.

The culture medium (2.5 ml) was then replaced:
either with test medium containing TGF-β (Transforming Growth Factor β) at 10 ng/ml (positive control),
or with test medium containing the essential oil of Example 1 at 0.003% by volume,
or with the same culture medium (control).

The cells were then incubated for 72 hours at 37° C.

The culture medium was removed and the cells were rinsed, fixed and permeabilized. They were then labelled with an Anti-Collagen IV primary antibody sold by Abcam (reference: Ab6586) directed against the protein of interest (collagen IV). This antibody was visualized with an Alexa Fluor® 488 Goat Anti-Rabbit IgG (H+L) secondary antibody sold by Invitrogen (reference: A11008) coupled to a fluorochrome (GAR-Alexa 488). In parallel, the nuclei of the cells were stained with Hoechst 33258 (bisbenzimide).

The image acquisition was carried out with an INCellAnalyzer™1000 (GE Healthcare) high-resolution imaging system. For each well, 5 digitized images were acquired.

The labellings were quantified by measuring the fluorescence intensity of the proteins relative to the number of nuclei identified by the Hoechst product (integration of the digital data using the Developer Toolbox 1.5 software, GE Healthcare).

Results—Conclusion

FIG. 1 represents the collagen IV produced by the control keratinocytes.

FIG. 2 represents the collagen IV produced by the keratinocytes treated with TGF-β (tested at 10 ng/ml). This is the positive control of the experiment.

FIG. 3 represents the collagen IV produced by the keratinocytes treated with the essential oil of *Achillea* (tested at 0.003%).

Figure 1:
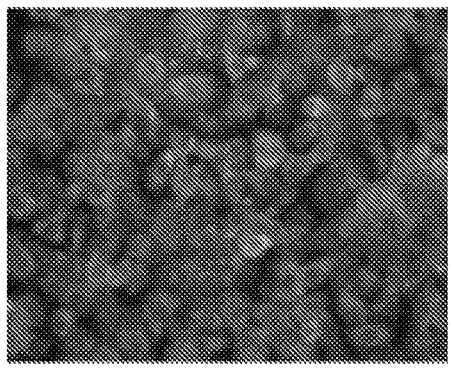
FIGS. 1 to 3 represent the fluorescence microscopy images obtained after collagen IV-immunolabelling of keratinocytes according to the protocol described above.
Figure 2:
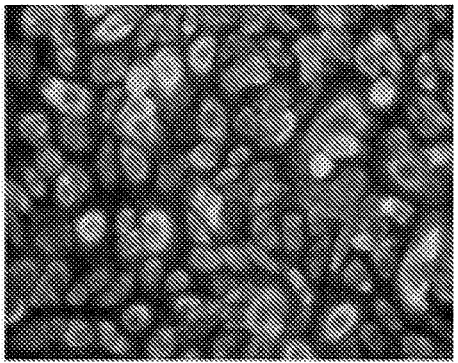
Figure 3:
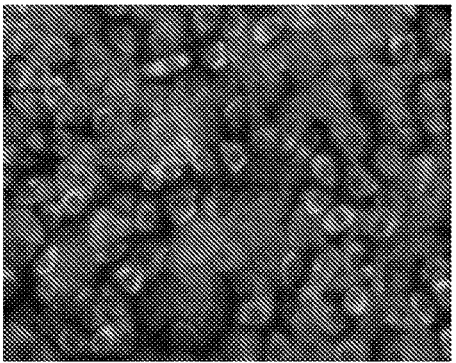

TGF-β (tested at 10 ng/ml) very strongly and significantly stimulated collagen IV production by the keratinocytes (594% relative to the control). This effect was expected and validates the test.

Under the experimental conditions of this study, the essential oil of *Achillea* (tested at 0.003%) significantly stimulated collagen IV expression (171% relative to the control) by the keratinocytes.

Thus, the essential oil of *Achillea* in accordance with the invention makes it possible to increase collagen IV production by keratinocytes and, consequently, to prevent and/or treat the signs of skin ageing.

Example 3: Effect of an Essential Oil of *Achillea* on Intra-Tissue Glutathione Concentration The present example aims to show that the essential oil of *Achillea* makes it possible to increase the intra-tissue glutathione concentration.

For this, the GSH level was measured in the epidermis of a Realskin™ reconstructed skin which was:

nontreated (control), treated with essential oil of *Achillea* at 0.01% by volume, or treated with lipoic acid at 250 µmol·l$^{-1}$ (positive control).

Procedure:

The reconstructed tissue model kits are conditioned for transport on agar medium. Upon arrival, the tissues were reconditioned in a maintenance medium for a minimum of 16 h at 37° C. in a moisture-saturated atmosphere enriched with 5% $CO_2$. The same medium was used for the incubations in the presence of the substrate.

The various solutions (2 ml) (of essential oil of *Achillea* at 0.01% by volume and of lipoic acid at 250 mmol·l$^{-1}$) were deposited in the wells underneath the skins in order to diffuse through said skins more easily by capillary action. The tissues were then incubated in an incubator at 37° C. for 16 h.

The tissues were ground by means of a Potter grinder in 250 ml of a solution of N-ethylmaleimide (NEM) at 2.5 mmol·l$^{-1}$ (excess of NEM). The Potter grinder was then washed with 250 ml of ultrapure water, and 500 µl of 2% formic acid were added. The samples were then centrifuged for 15 minutes at 6000 rpm and at 4° C.

In order to assay the glutathione coupled to the NEM (GS-NEM), 25 ml of the supernatant is diluted in 975 µl of 1% formic acid (1/40) in a 1 ml vial. It is then assayed relative to a range of increasing concentrations of GS-NEM (50-100-200-300-400-500-600 nmol·l$^{-1}$) prepared from a stock solution of GS-NEM at 1 mmol·l$^{-1}$ (3.1 mg of GSH, i.e. 10 µmol in 10 ml of a solution of NEM at 2.5 mmol·l$^{-1}$). All of the analyses were carried out by LC/MS (Thermo Fisher Quantum ultra AM triple quadrupole mass spectrometer).

Results—Conclusion:

It was observed that the treatment of the tissues with solutions of oil of *Achillea* (0.01% by volume) and of lipoic acid (250 mmol·l$^{-1}$) results respectively in an increase in the GSH level of 26.8+/−6.1% and 52.0+/−12.7% relative to the nontreated tissues.

Since lipoic acid is known to increase the GSH level, this test makes it possible to validate the experiment.

Thus, the essential oil of *Achillea* in accordance with the invention makes it possible to increase the intra-tissue glutathione concentration and, consequently, to prevent and/or treat the signs of skin ageing.

Example 4: Composition

Face Cream

| Ingredients | Percentage by weight relative to the total weight of the composition |
|---|---|
| Powdered potassium sorbate | 0.1 |
| Xanthan: polysaccharides: glucose/mannose/glucuronic acid (40/30/30) | 0.3 |
| Mixture of plant origin of lecithin, fatty acids and alcohols | 5 |
| Essential oil of *Achillea* according to Example 1 | 0.5 |
| First cold-pressed bio sunflower oil | 20 |
| Glyceryl stearate citric ester | 2 |
| Benzyl alcohol (and) dehydroacetic acid (and) water | 0.8 |
| Fragrance | 0.45 |
| Citric acid | 0.1 |
| Water | qs 100 |

The invention claimed is:

1. Cosmetic method for preventing and/or treating the signs of skin ageing, comprising applying a composition to a subject in need thereof comprising from 0.05% to 0.8% by weight relative to the total weight of the cosmetic composition of an essential oil of *Achillea*, as an active agent, wherein this essential oil of *Achillea* comprises the following compounds, each present at more than 5% by weight relative of the total weight of the essential oil:
    *artemisia* ketone,
    chrysanthenone (two combined isomers), and
    ascaridole.
2. Cosmetic method according to claim 1, of an essential oil of *Achillea* also comprising the following compounds:
    para-cymene,
    1,8-cineole and beta-phellandrene, and
    camphor.
3. Cosmetic method according to claim 1, of an essential oil of *Achillea* comprising the following compounds, each present at more than 6% by weight relative to the total weight of the essential oil:
    *artemisia* ketone,
    chrysanthenone (two combined isomers), and
    ascaridole.
4. Cosmetic method according to claim 1, of an essential oil, in which the following compounds are each present at concentrations of greater than 1% by weight relative to the total weight of the essential oil:
    camphene,
    yomogi alcohol,
    alpha-thujone,
    artemisyl acetate, and
    isoascaridole.
5. Cosmetic method according to claim 1, wherein the essential oil of *Achillea* is obtained from the aerial part of *Achillea*.
6. Cosmetic method according to claim 1, said signs of skin ageing being chosen from wrinkles and/or fine lines, dull and lifeless skin, thinning of the skin, loss of firmness and/or of elasticity and/or of tonicity and/or of suppleness of the skin and/or slackening of the skin.
7. Cosmetic method according to claim 1, said signs of skin ageing being induced by extrinsic ageing, or induced by chronological ageing.
8. Cosmetic method according to claim 1, in which said essential oil of *Achillea* is present in a cosmetic composition.
9. Cosmetic method according to claim 8, wherein said composition is intended for topical or oral administration.
10. Cosmetic method according to claim 8, in which the essential oil is formulated in an anti-ageing cream.
11. Cosmetic process for preventing and/or treating the signs of skin ageing, comprising at least one step of topical application to the skin of a composition comprising at least one essential oil of *Achillea*, as defined according to claim 1.

* * * * *